United States Patent [19]
Dow et al.

[11] Patent Number: 5,639,757
[45] Date of Patent: Jun. 17, 1997

[54] 4-AMINOPYRROLO[2,3-D]PYRIMIDINES AS TYROSINE KINASE INHIBITORS

[75] Inventors: Robert L. Dow, Waterford; Kevin Koch, Stonington, both of Conn.

[73] Assignee: Pfizer Inc., New York, N.Y.

[21] Appl. No.: 448,248

[22] Filed: May 23, 1995

[51] Int. Cl.$^6$ .......................... A61K 31/505; A61K 31/52
[52] U.S. Cl. ..................... 514/261; 514/258; 514/260; 514/259
[58] Field of Search ......................... 514/261, 258, 514/260, 259

[56] References Cited

U.S. PATENT DOCUMENTS

| | | | |
|---|---|---|---|
| 5,036,071 | 7/1991 | Johansson et al. | 514/261 |
| 5,457,105 | 10/1995 | Barker | 514/234.5 |
| 5,475,001 | 12/1995 | Barker | 514/258 |

OTHER PUBLICATIONS

Chemical Abstracts 111:39290e, "Synthesis and Biological Activity of Pyrrolo [2,3-d] Pyrimidines", Dave et al. Aug. 1988.

Chaitanya, G. Dave. *Indian Journal of Chemistry* vol. 27B, Aug. 1988, pp. 778–780, "Synthesis & Biological Activity of Pyrrolo[2,3–d]pyrimidinest".

Chaitanya, G. Dave. *Indian Journal of Chemistry* 64, 713 (1987) pp. 713–715, "Pyrrolo[2,3–d]pyrimidines. Synthesis and Reaction of 2–Amino-3–cyanopyrroles".

*Primary Examiner*—Frederick Krass
*Attorney, Agent, or Firm*—Peter C. Richardson; Gregg C. Benson; A. Dean Olson

[57] ABSTRACT

Certain 4-aminopyrrolo[2,3-d]pyrimidine compounds, and their pharmaceutically-acceptable salts, are inhibitors of tyrosine kinase enzymes, and are useful for immunoregulation and for the treatment of cancer, angiogenesis and atherosclerosis.

7 Claims, No Drawings

4-AMINOPYRROLO[2,3-D]PYRIMIDINES AS TYROSINE KINASE INHIBITORS

This invention relates to the use of 4-amino-pyrrolo[2,3-d]pyrimidine compounds which are tyrosine kinase inhibitors, pharmaceutical compositions containing such tyrosine kinase inhibitors, and the use of such tyrosine kinase inhibitors for the treatment of tyrosine kinase dependent diseases/conditions such as autoimmune diseases, graft rejection, cancer, angiogenesis or atherosclerosis, in mammals.

BACKGROUND OF THE INVENTION

The pyrrolo[2,3-d]pyrimidines of this invention are described in the following publications: "Pyrrolo[2,3-d]pyrimidines Synthesis and Reaction of 2-Amino-3-cyanopyrroles" Journal of Indian Chemical Society 64, 713 (1987) Chaitanya G. Dave, P. R. Shah, and S. P. Upadhyaya; and "Synthesis and Biological Activity of Pyrrolo[2,3-d]pyrimidines" Indian Journal of Chemistry, Vol. 27B, August 1988, pp. 778–780. Chaitanya G. Dave, P. R. Shah, and S. P. Upadhyaya.

Tyrosine-specific protein kinases (tyrosine kinases) represent a family of enzymes which catalyze the transfer of the terminal phosphate of adenosine triphosphate to tyrosine residues in protein substrates. The first members of this class to be identified were tyrosine kinases associated with viral genes (termed oncogenes) which were capable of cell transformation (i.e. pp60v-src and pp98v-fps). Later it was shown that there were normal cellular counterparts (i.e. pp60c-src and pp98c-fps) to these viral gene products. A third category of tyrosine kinases to be identified are those termed the growth factor receptors, which includes insulin, epidermal growth factor, and p185HER-2 receptors. All of these tyrosine kinases are believed, by way of substrate phosphorylation, to play critical roles in signal transduction for a number of cell functions.

Though the exact mechanisms of signal transduction have yet to be elucidated, tyrosine kinases have been shown to be important contributing factors in cell proliferation, carcinogenesis and cell differentiation. Therefore, inhibitors of these tyrosine kinases are useful for the prevention and chemotherapy of proliferative diseases dependent on these enzymes.

For example, tyrosine kinase inhibitors are useful for inhibiting T-cell proliferation and thus they are useful as immunosuppressive agents for the prevention or treatment of graft rejection following transplant surgery and for the prevention or treatment of autoimmune diseases such as rheumatoid arthritis and psoriasis.

Graft or transplant rejection following transplant surgery is a common occurrence which arises when foreign antigens are recognized by the host's immune response system. Then, the host's immune response system, in an effort to "protect" itself from the foreign tissue, releases its arsenal of antibodies and soluble lymphokines which amplify the immunologic response. The antibodies attack the foreign tissue, resulting in complications which often end in rejection of said tissue.

Similarly, the occurrence of immunoregulatory irregularities in autoimmune and chronic inflammatory diseases is well known. Irrespective of the underlying etiology of the condition, a variety of autoantibodies and self-reactive lymphocytes often arise to complicate or perpetuate the condition.

Treatments which target the immune response system often result in a complete shutdown of the system, leading to a lowering of the body's ability to combat infection. This can be as dangerous as the original condition which led to the shutdown.

Currently the leading medicinal agent for the prevention or treatment of graft rejection is cyclosporin A, approved by the United States Food and Drug Administration in 1983. The drug acts by inhibiting the body's immune response system from mobilizing its arsenal of natural protecting agents to reject the transplant's foreign protein. Although cyclosporin is effective in fighting graff rejection, it suffers drawbacks in that it can cause kidney failure, liver damage and ulcers; which in many cases can be very severe. Safer drugs which are more selective in their ability to affect the immune response system and which have fewer side effects are constantly being pursued.

Thus, although there are a variety of therapies for treating tyrosine kinase dependent diseases there is a continuing need and a continuing search in this field of art for alternative therapies.

SUMMARY OF THE INVENTION

This invention is directed to a method of treating tyrosine kinase dependent diseases/condition which comprises administering to a mammal suffering from a tyrosine kinase dependent disease/condition a tyrosine kinase dependent disease/condition treating amount of a compound of Formula I

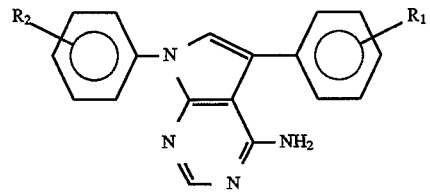

or a pharmaceutically acceptable anionic salt thereof wherein $R_1$ and $R_2$ are each independently H, halo, alkyl($C_1$–$C_4$), or alkyloxy($C_1$–$C_4$).

Preferred compounds of Formula I are those compounds wherein $R_1$ and $R_2$ are each independently H, bromo, chloro, iodo, methyl or methoxy.

Within this group of preferred compounds of Formula I are especially preferred compounds wherein $R_1$ and $R_2$ are each in the para position.

It is especially preferred that about 0.1 to 20 mg/kg of body weight of the Formula I compound is used daily.

Tyrosine kinase dependent diseases or conditions refers to hyperproliferative disorders which are initiated/maintained by aberrant tyrosine kinase enzyme activity. Examples include cancer, atherosclerosis and angiogenesis (e.g., tumor growth, diabetic retinopathy). Other examples include immunoregulation (graft rejection), psoriasis and rheumatoid arthritis.

The term "treating" as used herein includes preventative (e.g., prophylactic) and paliative treatment.

By halo is meant chloro, bromo, iodo, or fluoro.

By alkyl is meant straight chain or branched saturated hydrocarbon.

The expression "pharmaceutically-acceptable anionic salt" refers to non-toxic anionic salts containing anions such as, but not limited to, chloride, bromide, iodide, sulfate, bisulfate, phosphate, acetate, maleate, fumarate, oxalate, lactate, tartrate, citrate, gluconate and 4-toluene-sulfonate.

As used herein, the expression "reaction-inert solvent" refers to a solvent which does not interact with starting materials, reagents, intermediates or products in a manner which adversely affects the yield of the desired product.

Other features and advantages will be apparent from the specification and claims.

DETAILED DESCRIPTION OF THE INVENTION

The method of preparation of compounds of Formula I are well known to those skilled in the art and are described in the following journal articles:

Pyrrolo[2,3-d]pyrimidines. Synthesis and Reaction of 2-Amino-3-cyanopyrroles. Journal of Indian Chemical Society 64, 713 (1987) Chaitanya G. Dave, P. R. Shah, and S. P. Upadhyaya;

Synthesis and Biological Activity of Pyrrolo[2,3-d] pyrimidines. Indian Journal of Chemistry, Vol. 27B, August 1988, pp. 778–780. Chaitanya G. Dave, P. R. Shah, and S. P. Upadhyaya.

The compounds of this invention are basic and they form acid salts. All such acid salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The starting materials for the above described compounds/reagents (e.g., the salts, acid halides, acid anhydrides) can be easily synthesized by those skilled in the art starting from common chemical reagents using conventional methods of organic synthesis.

The compounds of this invention are all readily adapted to therapeutic use as tyrosine kinase inhibitors for the treatment of tyrosine kinase dependent diseases/conditions in mammals (e.g., human). Tyrosine kinase dependent diseases or conditions refers to hyperproliferative disorders which are initiated/maintained by aberrant tyrosine kinase enzyme activity. Examples include psoriasis, cancer, immunoregulation (graff rejection), atherosclerosis, angiogenesis (e.g., tumor growth, diabetic retinopathy), etc.

The compounds of this invention are particularly useful in the treatment of resistance to transplantation and autoimmune diseases such as rheumatoid arthritis or psoriasis. In the treatment of resistance to transplantation, a compound of this invention may be used either prophylactically or in response to an adverse reaction by the human subject to a transplanted organ or tissue. When used prophylactically, a compound of this invention is administered to the patient or to the tissue or organ to be transplanted in advance of the transplantation operation. Prophylactic treatment may also include administration of the medication after the transplantation operation but before any signs of adverse reaction to transplantation are observed. When administered in response to an adverse reaction, a compound of this invention is administered directly to the patient in order to treat resistance to transplantation after outward signs of the resistance have been manifested.

For use in the treatment of tyrosine kinase dependent diseases/conditions (e.g., resistance to transplantation and autoimmune diseases (e.g., rheumatoid arthritis or psoriasis)) in a mammal, including a human, a compound of this invention may be formulated into a suitable pharmaceutical composition containing a tyrosine kinase disease or condition treating effective amount. Depending upon the potency of the particular compound of this invention being administered, about 0.05 mg/kg per day to about 30 mg/kg per day per body weight of the mammal, in single or multiple daily doses, is the amount administered. A more preferred range is 0.10 mg/kg per day to about 20 mg/kg per day per body weight of the mammal, although in particular cases, at the discretion of the attending physician, doses outside the broader range may be required. In any event the amount and timing of compound(s) administered will, of course, be dependent on the subject being treated, on the severity of the affliction, on the manner of administration and on the judgment of the prescribing physician.

Generally, the compounds of this invention are administered orally, but parenteral administration (e.g., intravenous, intramuscular, subcutaneous or intramedullary) may be utilized, for example, where oral administration is inappropriate for the instant target or where the patient is unable to ingest the drug. Topical administration may also be indicated, for example, where the patient is suffering from a skin disease such as psoriasis or whenever the medication is best applied to the surface of a tissue or organ as determined by the attending physician.

The compounds of the present invention are generally administered in the form of a pharmaceutical composition comprising at least one of the compounds of this invention together with a pharmaceutically acceptable vehicle or diluent. Thus, the compounds can be administered individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of topical administration, dilute sterile, aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples, see *Remington's Pharmaceutical Sciences*, Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the subject being treated, i.e., a tyrosine kinase dependent disease.

The utility of the compounds of the present invention as medical agents in the treatment of resistance to transplantation and autoimmune diseases such as rheumatoid arthritis or psoriasis is demonstrated by the activity of the compounds of this invention in the biological assay described below. This biological assay also provides a means whereby the activities of the compounds of the present invention can be compared with the activities of other known compounds. The results of these comparisons are useful for determining dosage levels in mammals, including man, for the treatment of resistance to transplantation and autoimmune diseases such as rheumatoid arthritis and psoriasis.

The human mixed lymphocyte reaction (MLR) is used to generate an immune response in vitro which is measured via $^3$H-thymidine uptake. This assay uses peripheral blood mononuclear cells in a modified two-way MLR. To ensure disparity of HLA type D antigens and therefore maximize stimulation, a pool of frozen donor cells is used as the stimulator population; freshly isolated cells are used as the responder population.

Freshly drawn mononuclear cells are suspended in RPMI-1640 tissue culture (Sigma, Inc.) enriched with: 0.5% MEM non-essential amino acids (100×) solution, 1% L-glutamine (200 mM), 1% MEM vitamins (100×), 1% penicillin streptomycin solution (10,000 units/mL) and 15% heat-inactivated human AB serum (NABI). The cells are counted and the concentration is adjusted to $5 \times 10^5$ cells/mL. The solution is then transferred to round bottom 96 well plates in 100 µL/well quantities. These plates contain the responder cells.

The stimulator cells are prepared by pooling the mononuclear cells collected from several different individuals. The cells are suspended in 90% human AB serum and 10% DMSO such that the cell count is $2 \times 10^7$ cells/mL. The cells are stored in liquid nitrogen. For an MLR, the viable cells are diluted to $5 \times 10^5$ cells/mL, and 100 µL/well is added to the plates containing the responder cells. To each well, containing a mixture of responder cells and stimulator cells, is added 50 µL of compound solution. Triplicate wells are run for each dose. The plates are incubated at 37° C. under an atmosphere of 5% $CO_2$ and are humidified for five days. To each well is added 1 µC of $^3$H-thymidine and incubation is continued for another eighteen hours. The cells are harvested using a Beta Plate system (Wallac Inc., Gaithersburg, Md).

The percent inhibition of stimulated control is obtained using the following equation:

$$\% \text{ Inhibition} = \left[ 1 - \left( \frac{\text{avg. cpm of drug}}{\text{avg. cpm of stimulated control}} \right) \right] \times 100$$

The abbreviation cpm is defined as counts per minute.

Activity in the MLR screen recited above is indicative of usefulness of the active compound in the treatment of resistance to transplantation and autoimmune diseases such as rheumatoid arthritis and psoriasis.

The utility of the compounds of the present invention as medical agents in the treatment of tyrosine kinase dependent diseases is further demonstrated by the activity of the compounds of this invention in the biological assays described below. The biological assays also provide a means whereby the activities of the compounds of this invention can be compared with the activities of other known compounds. The results of these comparisons are useful for determining dosage levels in mammals, including man, for the treatment of tyrosine kinase dependent diseases such as cancer, atherosclerosis, antiangiogenesis, graft rejection, rheumatoid arthritis or psoriasis.

The in vitro tyrosine kinase inhibitory activity of the compounds of this invention may be demonstrated by methods based on standard procedures. The in vitro tyrosine kinase inhibitor activity of the present compounds may be demonstrated by a method in which an immune complex kinase assay (ICKA) is used to assess the specificity of tyrosine kinase inhibitors against a panel of Src-family protein tyrosine kinases (PTK).

96-well assay plates are coated with enolase (100 ul) (Sigma Corp., St. Louis, Mo.) for the 1 h at 37° C. and then blocked with 300 ul 0.5% BSA. A cell lysate containing the kinase of interest is prepared. The kinase of interest is produced by the baculovirus expression system in cells. The cells are lysed in 0.5 NP-40, 0.02% Tris, 150 mM NaCl and 1% aprotinin. The kinase is immunoprecipitated from the lysate with the appropriate antibody and subsequent incubation with protein-A coated Sepharose (Sigma, Inc.) beads. The beads are washed four times in a 1:10 bead to wash buffer volume ratio. They are resuspended to their final volume in kinase buffer and then aliquoted with an Eppendoff repeater piper into appropriate assay wells. (Kinase buffer = 25 mM HEPES, 3 mM MnC12, 0.1 mM $Na_3VO_4$). Compounds of this invention and gamma-32P-ATP are then added to assay wells. After the final 20 min incubation, the assay wells are washed with a 1 mM ATP/50 mM EDTA buffer in two 9 sec wash cycles on a Microcell 96 Harvester (Skatron Instruments, Sterling, Va).

Scintillant is added to each well and the plate is read on a Micro-Beta Wallac, Inc. (Gaithersburg, Md.) reader. Generally, only alternate rows on an assay plate are used due to the inability of the crosstalk correction program of the Micro-Beta to correct for the high energy beta in adjacent wells. Samples are run in triplicate, averaged and then plotted to determine an $IC_{50}$.

In another method the enzyme pp60src, a tyrosine-specific phosphokinase (tyrosine kinase) associated with the inner surface of the plasma membrane, is purified from Rous sarcoma virus-transformed rat cells. In the basic assay the enzyme is incubated with the substrate (6 mg/mL), va15 angiotensin II, and 20 µM gamma-32p-ATP in a total volume of 25 µl for 25 minutes at 30° C. according to Wong, T. W., Goldberg, A. R. *J. Biol, Chem.*, 259, 8505–8512 (1984). The reaction is terminated by the addition of 45 µl of 5% TCA, incubated on ice for 5 minutes and centrifuged for 1 minute to remove precipitated protein. 35 µl aliquots of the supernatants are applied to phosphocellulose paper circles, which are then washed in 3 changes of 0.5% $H_3PO_4$, acetone-rinsed, dried and counted by liquid scintillation. For screening, the compound to be tested is included in the 25 µl incubation mixture; compounds are tested at $10^{-4}$M, $10^{-5}$M and $10^{-6}$M and appropriate solvent controls are included in all assays.

EXAMPLES 1–15

The enzyme pp60src, a tyrosine-specific phosphokinase (tyrosine kinase) associated with the inner surface of the plasma membrane, was purified from Rous sarcoma virus-transformed rat cells. In the basic assay the enzyme was incubated with the substrate, 6 mg/mL va15 angiotensin II, and 20 µM gamma-32p-ATP in a total volume of 25 µl for 25 minutes at 30° C. according to Wong, T. W., Goldberg, A. R., *J. Biol. Chem.*, 259, 8505–8512 (1984). The reaction was terminated by the addition of 45 µl of 5% TCA, incubated on ice for 5 minutes and centrifuged for 1 minute to remove precipitated protein. 35 µl aliquots of the supernatants were applied to phosphocellulose paper circles, which were then washed in 3 changes of 0.5% $H_3PO_4$, acetone-rinsed, dried and counted by liquid scintillation. For assaying, the compound to be tested was included in the 25 µl incubation mixture; compounds were tested at $10^{-4}M$, $10^{-5}M$ and $10^{-6}$ and appropriate solvent controls were included in all assays.

The compounds of Formula I wherein $R_1$ and $R_2$ are as detailed in Table 1 (below) were tested in the above biological assay and were found active.

TABLE 1

| Example No. | $R_1$ | $R_2$ |
| --- | --- | --- |
| 1 | H | methoxy |
| 2 | chloro | iodo |
| 3 | chloro | H |
| 4 | methyl | chloro |
| 5 | methyl | bromo |
| 6 | H | iodo |
| 7 | methyl | H |
| 8 | chloro | methoxy |
| 9 | methoxy | methoxy |
| 10 | methyl | iodo |
| 11 | methoxy | bromo |
| 12 | chloro | bromo |
| 13 | chloro | methyl |
| 14 | methyl | methoxy |
| 15 | methoxy | iodo |

It should be understood that the invention is not limited to the particular embodiments described herein, but that various changes and modifications may be made without departing from the spirit and scope of this novel concept as defined by the following claims.

We claim:

1. A method of treating tyrosine kinase dependent diseases which comprises administering to a mammal suffering from cancer, atherosclerosis, angiogenesis, graft rejection, rheumatoid arthritis or psoriasis a cancer, atherosclerosis, angiogenesis, graft rejection, rheumatoid arthritis or psoriasis treating amount of a tyrosine kinase inhibitor compound of Formula I:

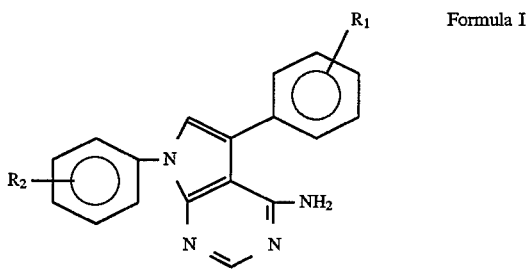

Formula I or a pharmaceutically-acceptable anionic salt thereof wherein $R_1$ and $R_2$ are each independently H, halo, alkyl ($C_1$–$C_4$), or alkyloxy ($C_1$–$C_4$) and inhibiting cancer, atherosclerosis, angiogenesis, graft rejection, rheumatoid arthritis or psoriasis dependent tyrosine kinases.

2. The method as recited in claim 1 wherein $R_1$ and $R_2$ are each independently H, halo, alkyl ($C_1$–$C_4$), or alkyloxy ($C_1$–$C_4$) and the tyrosine kinase is pp60src.

3. The method as recited in claim 1 where $R_1$ and $R_2$ are each in the para position.

4. The method as recited in claim 2 wherein $R_1$ and $R_2$ are each in the para position.

5. The method as recited in claim 2 wherein the amount is from about 0.1% to 20 mg/kg of body weight daily.

6. The method as recited in claim 5 wherein the tyrosine kinase dependent disease/ is graft rejection, atherosclerosis, angiogenesis or psoriasis.

7. The method as recited in claim 5 wherein the tyrosine kinase dependent disease is cancer or rheumatoid arthritis.

* * * * *